United States Patent [19]

Buchsbaum et al.

[11] Patent Number: 4,831,122
[45] Date of Patent: May 16, 1989

[54] RADIOIMMUNOTOXINS

[75] Inventors: Donald J. Buchsbaum, Minnetonka; Daniel A. Vallera, Minneapolis, both of Minn.

[73] Assignee: Regents of the University of Minnesota, Minneapolis, Minn.

[21] Appl. No.: 817,398

[22] Filed: Jan. 9, 1986

[51] Int. Cl.[4] .................. C07K 15/00; A61K 39/44
[52] U.S. Cl. .................. 530/389; 530/390; 530/391; 530/808; 424/1.1; 424/85.91; 128/1.1; 514/885; 435/68
[58] Field of Search ............... 530/391, 370, 389, 808; 424/85, 1.1; 514/885; 435/68

[56] References Cited

U.S. PATENT DOCUMENTS

| | | |
|---|---|---|
| 4,359,457 | 11/1982 | Neville, Jr. et al. |
| 4,414,148 | 11/1983 | Jansen et al. |
| 4,460,559 | 7/1984 | Goldenberg |
| 4,474,893 | 10/1984 | Reading |
| 4,500,508 | 2/1985 | Srivastava et al. |
| 4,520,226 | 5/1985 | Neville, Jr. et al. |
| 4,545,985 | 10/1985 | Pastan et al. |
| 4,550,086 | 10/1985 | Reinherz et al. |
| 4,642,334 | 2/1987 | Moore et al. ............ 530/391 |
| 4,664,911 | 5/1987 | Uhr et al. ............... 424/85 |
| 4,671,958 | 6/1987 | Rodwell et al. ......... 530/391 |
| 4,707,352 | 11/1987 | Stavrianpoulos ........ 424/89 |

FOREIGN PATENT DOCUMENTS 0173629 3/1986 European Pat. Off.
0175617 3/1986 European Pat. Off.

OTHER PUBLICATIONS

CA, vol. 105, 1986, #38354t, Muroi.
CA, vol. 102, 1985, #216596w, Shimoda et al.
CA, vol. 100, 1984, #119074a, Strand et al.
Hnatowich et al., Science 220, 1983, pp. 613-615.
Reilly et al, Can. J. Hospital Pharm., vol. 40, 1987, pp. 209-214.
"Monoclonal Antibody Conjugates for Tumor Imaging & Therapy", Strand et al, Cell Fusion: Gene Transfer & Transformation, Raven Press, pp. 385-393 (1984).
"Diagnostic Imaging and Therapy Using Monoclonal Antibodies in Erythroleuhemic Mice", Strand et al, Radioimmunoimaging & Radioimmunotherapy, pp. 243-254 (1983).
"Monoclonal Antibody Conjugates for Diagnostic Imaging and Therapy", Strand et al, Monoclonal Antibodies & Cancer, Academic Press, pp. 125-131 (1983).
Daniel A. Vallera, "The Use of Immunotoxins and Bone Marrow Transplantation: Eradication of T Cells and Leukemic Cells" (1985).
St. Paul Pioneer Press and Dispatch, Sep. 11, 1985, p. 14D; Aug. 14, 1985, p. 2A.
By Vitetta and Uhr from Ann. Rev. Immunol., "Immunotoxins", 3:197-212 (1985).
By Weil-Hillman et al, Cancer Research 45, "Cytoxic Effect of Anti-$M_r$ 67,000 Protein Immunotoxin on Human Tumors in a Nude Mouse Model", pp. 1328-1336, Mar. 1985.
Minneapolis Star and Tribune, Dec. 29, 1983.
Business Week May 18, 1981 at p. 156.
Science, vol. 222, Vallera et al, "Anti-T-Cell Reagents for Human Bone Marrow Transplantation: Ricin Linked to Three Monoclonal Antibodies", pp. 512-515 (Nov. 4, 1983).
High Technology, "Monoclonal Antibodies: Promises Fulfilled", Feb. 1986, p. 35.
Blood, vol. 66, No. 33, "Use of Multiple T Cell-Directed Intact Ricin Immunotoxins for Autologous Bone Marrow Transplantation", by Strong et al, (Sep. 1985) pp. 627-635.
Cancer Research 44, Strong et al, "Elimination of Clonogenic T-Leukemic Cells from Human Marrow Using Anti-$M_r$ 65,000 Protein Immunotoxins", Jul. 1984, 3,000-3,006.

Primary Examiner—Johnnie R. Brown
Assistant Examiner—Garnette D. Draper
Attorney, Agent, or Firm—Vidas & Arrett

[57] ABSTRACT

Radioimmunotoxins consisting of a monoclonal antibody covalently coupled to a toxin and a radionuclide. The compositions retain high binding specificity and cytotoxic activity and are useful in treating cancer and in bone marrow transplantation. The antibody component determines the selectivity. The toxin component kills the targeted cells. The radionuclide component also kills, but by a different mechanism, thus ensuring the eradication of all tumor cells. The radionuclide also allows the radioimmunotoxin to be tracked in vivo which enables the determination of its distribution throughout the body. Also, the pharmacokinetics of injected radioimmunotoxin can be determined allowing for more exact dose quantitation and administration.

6 Claims, 3 Drawing Sheets

RADIOIMMUNOTOXINS

FIELD OF THE INVENTION

This invention relates to monoclonal antibodies, immunotoxins and more particularly, to radiolabeled immunotoxins, referred to herein as radioimmunotoxins (hereinafter RIT).

BACKGROUND OF THE INVENTION

The advent of hybridoma techniques has brought about the possibility of producing homogeneous populations of highly specific antibodies against a variety of antigens. These monoclonal antibodies have promise in the diagnosis and treatment of many diseases. Loss of antibody from the cell surface or failure of antibody alone to show therapeutic effects has posed a serious problem with regard to the potential usefulness of monoclonal antibodies (hereinafter MoAb) in clinical therapy.

Immunotoxins are hybrid molecules consisting of a MoAB covalently bound to a plant or bacterial toxin. One such toxin, ricin, is a glycoprotein consisting of an A chain, which is toxic, and a B chain. The A chain is not capable of binding or penetrating cell membranes unless bound to a B chain. Ricin B chain binds galactose receptors on the cell surface.

In order to use an immunotoxin (hereinafter IT) having ricin linked to a MoAb, lactose must be added to prevent ricin binding to galactose receptors on cells other than the targeted cells.

It has been found by the inventors that IT induce internalization of the MoAb-toxin conjugate, rather than shedding from the cell surface. In contrast, antibody alone can be shed. "Arming" MoAb by toxin and radionuclide conjugation may, therefore, solve problems currently encountered in attempts at therapy with MoAb alone. Thus, there may be an advantage in the clinical use of IT and RIT. IT's have been employed by the inventors as purgative reagents for bone marrow transplantation and may be used as therapeutic reagents for the treatment of solid tumors. In cancer therapy, it is important to selectively kill every cancerous cell which is not possible with the use of MoAbs alone. Even IT may not kill all tumor cells in larger tumors. Therefore, the additional killing effects of irradiation are desirable.

BRIEF SUMMARY OF THE INVENTION

The present invention is to a new class of pharmaceutical compounds known as radioimmunotoxins or RIT. Radioimmunotoxins consist of a potent toxin, a monoclonal antibody and a radionuclide, all of which are linked together forming a highly specific and toxic killer of cells. The RIT's of the invention have a toxicity activity of at least 2 logs, a 99% kill rate. RIT's are useful in the treatment of cancer directly and indirectly. When used directly, the RIT's can selectively kill tumor cells that bear the determinant reactive with the monoclonal antibody. The toxin kills the cell to which the MoAb binds by protein synthesis inhibition. The radionuclide kills cells by the direct and indirect effects of ionizing irradiation on the DNA and cell proliferation capacity. Since irradiation may destroy cells in the immediate vicinity, the added effect of the radionuclide will insure that all cancerous cells are killed.

The presence of the radionuclide additionally permits the quantitation of the amount of toxin present. It enables one to localize and follow the biodistribution of the RIT within the tumor bearing host. After localization, it is possible to target the therapy to the exact site of the tumor. RIT may then be injected intratumorally, intravenously, intralymphatically or intraaterially to kill the tumor cells without killing normal cells. This is especially useful against inoperable solid tumors. Since toxins used in this therapy are extremely toxic, it is highly desirable to utilize only the quantity needed to avoid possible overkill. Localization and biodistribution pinpoints the target of the RIT's to be applied.

In the indirect approach, the RIT is extremely useful for treatment of graft versus host disease (GVHD) in bone marrow transplants for leukemia/lymphoma.

In regard to the indirect approach, radioimmunotoxins can be used for either autologous or allogeneic bone marrow transplantation. In autologous bone marrow transplantation, remission bone marrow cells from leukemia/lymphoma patients are frozen away and later returned to the patient. This approach is complicated by residual leukemia cells in the autologus graft which contribute to relapse. Preincubation of the autologous graft with radioimmunotoxins will eliminate the residual cancer cells. Radioimmunotoxins will also be extremely useful for treatment of graft-versus-host disease in human allogeneic bone marrow transplants for leukemia/lymphoma and other hematological disorders. Anti-T cell radioimmunotoxins will be useful for treatment of normal donor grafts to eliminate normal T lymphocytes. Normal donor T lymphocytes cause a pathological syndrome known as graft-versus-host disease, the most severe complication known in bone marrow transplantation in which donor T lymphocytes respond against recipient tissue.

In order to be useful, RIT must remain highly toxic and should not be rapidly eliminated from the blood following intravenous injection. RIT's must kill at a level of at least two logs (99% killed). Preferably, at least a 3 log kill rate (99.9%) or greater should be obtained. The RIT's of this invention retain specific cytotoxic activity and are eliminated relatively slowly from the blood.

Previous efforts to radiolabel immunotoxins have only been directed at quantitating the presence of IT on treated cells. These early efforts resulted in a loss of toxicity as reported by Vitetta and Uhr, in "Immunotoxins," *Ann. Rev. Immunol.*, 3:197–212 (1985). All activity of the labeled IT was lost. One of the instant inventors, Daniel A. Vallera, was a co-author of an article in *Science*, Vol. 222, pp. 512–515 (Nov. 4, 1983) entitled "Anti-T-Cell Reagents for Human Bone Marrow Transplantation: Ricin Linked to Three Monoclonal Antibodies." In that article, the authors describe the labeling of the ricin moiety of their immunotoxins with $^{125}I$ in order to determine the amount of ricin remaining in marrow after two hours of incubation and two washes. This study did not indicate biodistribution or whether the conjugate remained intact for more than a short period of time. The toxicity of the labeled moiety was never studied. However, since similar labeling was performed as above by Vitetta and Uhr, the toxin activity was presumably lost. Daniel Vallera did not consider the possibility that a radiolabeled immunotoxin itself may have advantages over the IT itself until his collaboration and co-invention with Donald Buchsbaum, a radiobiologist.

The RIT's of the invention have been found to be useful in therapy since they are more readily internalized than MoAb's. RIT's are not shed from the cell surface, in marked contrast to MoAb's.

BRIEF DESCRIPTION OF THE DRAWINGS

FIG. 1 shows protein synthesis inhibition on CEM or Daudi cells incubated with IT or RIT.

DETAILED DESCRIPTION OF THE INVENTION

I. Preparation of Radioimmunotoxin

A. Monoclonal Antibodies

Generally, any monoclonal antibody may be utilized in producing a radioimmunotoxin. All immunoglobulin subclasses are usable in this invention although the use of IgM may require a higher molar ratio of Iodine Monochloride or DTPA or SPDP to achieve the kill levels of IgM antibodies. A MoAb should be selected which is specific to the targeted cells and possesses little or no cross-reactivity to normal tissues. Typically, the MoAb to be used is specific to an intracellular or extracellular tumor associated antigen as a marker substance. These markers may be substances produced by the tumor or may be substances which accumulate within tumor cells, whether in the cytoplasm, the nucleus or in various organelles or subcellular structures. Tumor associated markers have been categorized in a number of categories including oncofetal, placental, oncogenic or tumor virus associated, tissue associated, and organ associated antigens. MoAb's may also be raised to cell surface antigens such as carcinoembryonic antigen (CEA).

Monoclonal antibodies may be produced by any of the methods which are well known in the art. Generally, MoAb's are produced by challenging an animal with a purified intracellular or extracellular marker, fusing antibody-producing animal lymph or spleen cells with myeloma cells to produce hybrid cells which are then isolated, cloned and selected for their ability to produce monoclonal antibodies specific to said marker substance.

The following represent some of the monoclonal antibodies useful for construction of radioimmunotoxins:

Anti-T cell/anti-T lineage leukemia: anti-CD1 (D-47, 4A76), anti-CD2 (35.1, OKT 11, 9.6, Campath 1), anti-CD3 (UCHT 1, OKT 3, 64.1), anti-CD4 (OKT 4, T4), anti-CD5 (T101, VIII-1, 10.2), anti-CD6 (12.1.5, T12/3Pt12B8), anti-CD7(3A-1, G3.7), anti-CD8 (OKT 8, T8).

Anti-B cell/anti-B lineage leukemia: anti-CD9 (BA-2), anti-CD-10 (BA-3), anti-CD24 (BA-1), pan-B (B43).

Myeloid: PM-81, AML-2-23, MCS-2.

Other monoclonals: anti-CEA, anti-melanoma, anti-breast, anti-lung, anti-prostrate, anti-pancreas, anti-brain, among others.

In the examples referred to herein, the monoclonal antibody T101, an IgG2a antibody which binds to peripheral blood T cells is utilized. T101 recognizes a 67,000-Dalton determinant on immature and mature normal T cells and T-cell leukemia lines. Specifically, the T101 MoAb from Hybritech, Inc., LaJolla, Calif. recognizes CD5, a glycoprotein cluster. T101 induces rapid modulation of CD5 and modulation is enhanced in the presence of monocytes.

B. Toxins

The toxins which are usable herein encompass all toxins used in the production of immunotoxins. Generally, the toxins include heterodimers made of a polypeptide chain (B chain) that binds the toxin to target cells via a sugar on the surface and a second chain (A chain) that displays enzymatic activity. The two chains are typically linked by a disulfide bond. Examples of two chain toxins are ricin, abrin, modeccin, diphtheria toxin and viscumin. However, single chain toxins, i.e. toxins composed of A chains only, e.g., gelonin, pseudomonas aeruginosa Exotoxin A, and amanitin may also be utilized. Other single chain toxins are hemitoxins which are also usable in this invention. They include pokeweed antiviral protein (PAP), saporin and momordin. Other useful single chain toxins include the A-chain fragments of the two chain toxins. A chain toxins with multiple B chains such as Shigella toxin are also usable in the invention.

As used herein, 2-chain toxins refers to toxins formed from two chains, and single chain toxins refers to both toxin obtained by cleaving 2-chain toxins as well as toxins having only one chain.

A preferred toxin is ricin, a toxic lectin extracted from the seeds of Ricinus communis, which contains an enzymatic and protein synthesis inhibiting A chain and a B chain which contains galactose binding site(s). Ricin is extremely toxic and it has been calculated that a single molecule of ricin in the cytosol will kill a cell.

Ricin may be obtained and purified by the procedures described in U.S. Pat. No. 4,340,535, the disclosure of which is incorporated herein by reference.

C. Radionuclides

Among the radionuclides used, gamma-emitters, positron-emitters, and X-ray emitters are suitable for localization and/or therapy, while beta emitters and alpha-emitters may also be used for therapy. Suitable radionuclides for forming the RIT of the invention include $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101m}$Rh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99m}$Tc, $^{11}$C, $^{13}$N, $^{15}$O and $^{18}$F.

D. Conjugation of MoAb to 2 Chain Toxins

For the conjugation of toxins having two chains (such as ricin) to a MoAb, a hetero bifunctional cross-linking reagent such as m-Maleimidobenzoyl-N-hydroxysuccinimide-ester (MBS) (Pierce Chemical Company) may be utilized. MoAb (0.5–5.0 mg at a concentration of about 4–6 mg/ml were first reduced with a freshly made solution of 1,4-dithiothreitol (DDT at 0.1 to 1 M) at room temperature for about thirty minutes. The final concentration is 10–100 mM DTT. Approximately 20 minutes following the reduction a freshly made solution of 48 mM MBS and N,N-dimethylformimide (DMF) is added to 1–16 milligrams of the toxin at a concentration of 10–12 milligrams/ml. This gave a final molar ratio of MBS to toxin equal to about 3:1. With ricin, the amount of DMF added should not exceed 10 microliters/ml of ricin in order to prevent denaturation of the protein.

Reduced antibody is purified from the DTT solution by passage through a G-25 superfine column (0.8×4–8 cm) equilibrated in 10 mM $Na_2HPO_4 \cdot 7H_2O$, 0.9% NaCl at pH 6.5–7.5. 5–8 drop fractions are collected from the column. A column of that size can effectively desalt a volume equivalent to approximately 15% of the G-25 resin. The absorbance at 280 nanometers was determined and the fractions with the highest readings were pooled. Protein concentration of the pooled fractions was determined. Recoveries from the G-25 column ranged from 50–75% depending on the initial amount of antibody conjugated.

Ricin was added to reduced antibody at a ratio of 7:1 to 18:1. The amount of ricin and antibody were chosen based on the recovery from the G-25 column. The molar ratios of reactants was claculated and the reduced antibody was added directly to the MBS/ricin mixture. The reaction was allowed to proceed at room temperature for 3 hours with occasional stirring.

After 3 hours, the reaction mixture was filtered through a Millipore GV, 0.22 micron filter prior to injection into a TSK SW3000 preparative HPLC column (21.5×600 mm ToyoSoda, Japan). The column was equilibrated in 100 mM $Na_2HPO_4 \cdot 7H_2O$, pH 7.2 at a flow rate of 2 ml/min. Antibody characteristically eluted by itself with a peak at 55–60 minutes. A successful conjugation was indicated by a peak of immunotoxin (antibody/ricin conjugate) eluting approximately 2–5 minutes before the antibody peak. Both the immunotoxin and unreacted antibody peaks were collected (approximately 35–45 ml) and stored at 4 degrees centigrade until further purification by affinity chromatography on Sepharose 4B resin.

A column of 1×10 cm containing Sepharose 4B was equilibrated in 100 mM $Na_2HPO_4 \cdot 7H_2O$, 150 mM NaCl, pH 7.5 at 4 degrees centigrade. Since any material containing ricin will bind to the Sepharose 4B by means of the galctose binding site of ricin B chain, the immunoconjugate bound to the column. The end reactive material is washed through the column by adding 5–10 ml of $Na_2HPO_4.7H_2O$ buffer. The absorbance is monitored at 280 nm and when the absorbance level returns to nearly the base line level, immunotoxin is eluted from the column by washing with buffer containing 50 mM lactose. The product is collected, filter sterilized and kept at 4 degrees centigrade or frozen at −70 degrees centigrade until use.

E. Conjugation of MoAb to Single Chain Toxins

Radioimmunotoxins can be made utilizing other toxins which are single polypeptide chains. Some, such as hemitoxins, have the advantage of not binding by means of a native receptor to human cells. The conjugation procedure employs the cross-linking reagent N-succinimidyl-3-(2-pyridyldithio)-propionate (SPDP, Pharmacia) which introduces a disulfide bond between the antibody and toxin moiety. The toxin (at least 5 mg/ml concentration) is first incubated with freshly made solution of SPDP (26 mM in N,N-dimethylformamide). The final molar ratio of SPDP to toxin is 3:1. The mixture is incubated for 30 minutes at room temperature with occasional stirring. SPDP modified toxin is purified from the reaction mixture by passage through a G-25 superfine column (0.8×4 cm) equilibrated with 40 mM $Na_2HPO_4 \cdot 7H_2O$, 150 mM NaCl at pH 6.5. The conjugated toxin is concentrated using an Amicon Centricon 10 microconcentrator. The concentration of toxin is determined by absorbance readings at 280 nanometers. The amount of antibody selected to give a final molar ratio of 3:1 toxin to antibody is then reacted for 30 minutes at room temperature with the amount of SPDP (6.5 mM) necessary to give a molar ratio of 3:1 SPDP to antibody. The antibody-SPDP reaction mixture is then passed over a G-25 superfine column equilibrated in 40 mM $Na_2HPO_4 \cdot 7H_2O$, 150 millimolar NaCl, at pH 7.5. During this time the SPDP modified toxin is reduced with 100 millimolar DTT at a final concentration of 5 mM DTT in order to release pyridyldithio groups. The reduction proceeds for 30 minutes at room temperature and then the toxin is purified from DTT by passage over a G-25 superfine column in $Na_2HPO_4 \cdot 7H_2O$ buffer, pH 7.5. The reduced and derivatized toxin is again concentrated using the Centricon 10 device and immediately mixed with SPDP modified antibody to give a final molar ratio of 3:1 toxin to antibody. Molecular weights of 29,000 to 30,000 daltons (toxin); 150,000 daltons (antibody); and 312 (SPDP) are used to calculate molar ratios.

The reaction proceeds overnight at 4° C. With occasional stirring before filtration and injection into the TSK SW 3000 preparative HPLC column (equilibrated with 100 mM $Na_2HPO_4 \cdot 7H_2O$, pH 7.2 at a flow rate of 2 ml/minute). Individual fractions are collected and contain mainly immunotoxin or antibody. Since these hemitoxins do not contain B chain binding site, they cannot be further purified on Sepharose 4B resin. The HPLC fractions are, therefore, assayed directly and kept frozen at −70° C. until use. This method is preferred for linking single chain toxins but can also be used for linking two chain toxins.

F. Radionuclide Labeling

The conjugated MoAb-toxin may then be labeled with a radionuclide. Alternatively, either the MoAb or toxin or both may be radiolabeled before conjugation.

1. Immunotoxin Labeling with Radionuclide

When the radionuclide of the RIT is an iodine isotope, the iodine monochloride micro method described by Contreras, MA; Bale, WF and Spar, I.L. in "Iodine monochloride (IC1) iodinatin techniques," *Methods in Enzymol* 92:277–292 (1983) must be utilized in order to create an RIT having a killing activity of 2 logs or greater. The chloramine-T method which has been widely used and described in patents to radiolabeled antibodies has been found to cause a loss of binding activity of the antibody and also a loss of toxicity of the toxin itself.

0.5 mg aliquots of immunotoxin have been labeled with mCi quantities of radioiodine and a 5:1 molar ratio of IC1 to immunotoxin to a specific activity of at least 0.5 mCi/mg without loss of antibody binding activity or toxin cytotoxicity.

The iodine monochloride micro method used is described below. The immunotoxin is dialyzed against borate buffer (0.16 M NaCl, 0.2 M $H_3BO_3$ and 0.04 M NaOH) adjusted to pH 8 with NaOH. This dialysis continues with a minimum of four changes of 20 volumes of the borate buffer, which is essential to remove reducing substances that would otherwise compete with the tyrosine residues for positive iodine. The dialysis tubing is pretreated by heating at 90 degrees centigrade in 0.05% EDTA, pH 7–8 with $NaHCO_3$ for 10 minutes, then copiously rinsed with distilled water and stored at 4 degrees centigrade in borate buffer. The iodination apparatus is a Reactivial (Pierce) with a triangular matrix teflon coated magnetic stir vane and teflon/silicon cap insert, which is rinsed with borate buffer. The vial with stir vane and protein in place is vented with a tuberculin syringe filled loosely with glass wool. Approximately 1 ml of protein solution at 0.5 mg/ml is used in a 3 ml vial.

The isotope $^{131}I$ or $^{125}I$ (Amersham) in the form of iodine ions (NaI) is diluted with borate buffer to 0.15 ml and added to the Reactivial with a 21 gauge needle and disposable syringe. Immediately, the vane is briefly and gently activated to mix protein and isotope. IC1 of an appropriate dilution from 0.02M stock (0.02M ICl, 2.0M NaCl, 0.02 M KCl and 1.0M HCl) is made with 0.85% NaCl, 0.015N HCl adjusted to 1 ml to give 5 equivalents of ICl per immunotoxin molecule. The IC1 is mixed immediately prior to addition to the Reactivial with the vane rotating briskly (avoid foaming). After 4–5 seconds the agitation is stopped and incorporation proceeds for one minute whereupon 1 ml of 5% human serum albumin is added as a protective protein against radiation damage, the contents mixed and the solution withdrawn with a 21 gauge needle and a disposable syringe. The protein solution is then passed over a Dowex 1-X4 resin (50–100 mesh Bio-Rad) ion exchange column of about 3 ml bed volume that has been prerinsed with 0.85% NaCl and 5% human serum albumin. The protein solution is followed by a 1 ml rinse of protective protein and then by 1 ml of 0.85% NaCl giving a final volume of 1.8 times the reaction volume.

The immunotoxin could be labeled with a variety of beta-emitting metallic radionuclides using the bicyclic anhydride of DTPA as the chelating agent. (Hnatowich, D.J. et al in "Radioactive Labeling of Antibody: A Simple and Efficient Method," *Science* 220:613–615 (1983) and Hnatowich, D.J. et al in "The Preparation of DTPA Coupled Antibodies Radiolabeled with Metallic Radionuclides: An Improved Method," *J. Immunol. Methods*, 65:147–157 (1983) describes suitable means which may be used in the radiolabeling of this invention.)

The DTPA is heated with an excess of acetic anhydride in pyridine for 24 hours. The anhydride is collected by filtration and washed repeatedly with acetic anhydride and dry ether. Characterization of the structure of the bicyclic anhydride is confirmed by infrared spectroscopy and melting point.

Coupling of the DTPA anhydride to monoclonal antibody or immunotoxin is carried out as follows: a 0.1 mg/ml solution of the DTPA anhydride in dry chloroform is prepared, and an aliquot containing the desired weight is added to the reaction test tube and evaporated to dryness at room temperature by a flow of nitrogen. A solution of 0.5 mg antibody or immunotoxin buffered at pH 7.0 with 0.05M bicarbonate buffer is added to the solid anhydride (7μg) for a 7:1 anhydride to protein molar ratio, and the solution is agitated for 1 minute. The coupled antibody is purified from free DTPA by passage through a 5 cm Sephadex G-50 gel filtration column. Fractions (1.0 ml) are collected from the G-50 column.

The fraction containing the highest concentration of protein is labeled with the beta-emitting radionuclide. Labeling is by ligand exchage, accomplished by adding a 0.5M acetate buffer solution of radionuclide to the reaction solution. The reaction vial is agitated for 5 minutes. The radionuclide-acetate solution is prepared by adding an equal volume of 1.0M acetate to the radionuclide-chloride solution, so that the final pH is 6.0. After the addition of radionuclide to the coupled protein solution, 0.1 ml of 25% human serum albumin is added to protect against radiation damage. The specific activity of the labeled antibodies or immunotoxins following dialysis to separate unbound radionuclide should be at least 0.5 mCi/mg.

Radiolabeling the antibody and toxin after coupling is preferred since there is greater retention of specific cytotoxic activity and a slower elimination of the reagent from the blood pool following intravenous injection. Another advantage is that since both the MoAb and toxin are radiolabeled, each can contribute to the death of malignant cells whether they are present on the cell surface (antibody) or internalized (antibody or toxin). Both the toxin and the antibody can be radiolabeled prior to immunotoxin synthesis.

2. Toxin Labeling

Ricin was labeled with $^{125}I$ by the lactoperoxidase labeling method (Thorell and Johansson, 1971), bound to a Sepharose 4B column and eluted with lactose to recover ricin with intact binding capacity. After labeled ricin was mixed with an appropriate amount of cold ricin, it was linked to TA1, UCHT1, and T101. Bone marrow mononuclear cells were pretreated for two hours under standard conditions and measured for gamma radioactivity.

TABLE 1

Binding of $^{125}TUT$ to Bone Marrow Mononuclear Cells[a]

|  | Total CPM | 1st Wash | | 2nd Wash | | Pellet | |
| --- | --- | --- | --- | --- | --- | --- | --- |
|  |  | CPM | % Total[b] | CPM | % Total | CPM | % Total |
| TUT mixture[c] | 2385 | 2289 | 96 | 68 | 3 | 140 | 6 |
| TA-1-ricin | 2185 | 2025 | 93 | 28 | 1 | 89 | 4 |
| UCHT-1-ricin | 2395 | 2319 | 97 | 23 | 1 | 93 | 4 |

TABLE 1-continued

| | Binding of $^{125}$TUT to Bone Marrow Mononuclear Cells[a] | | | | | | |
|---|---|---|---|---|---|---|---|
| | | 1st Wash | | 2nd Wash | | Pellet | |
| | Total CPM | CPM | % Total[b] | CPM | % Total | CPM | % Total |
| T101-ricin | 2790 | 2365 | 85 | 69 | 2 | 223 | 8 |

[a] Ricin was labeled with $^{125}$I by the lactoperoxidase method (1 mCi Na $^{125}$I/0.5 mg ricin). Labeled ricin was bound to a sepharose 4B column and eluted with 10 mM lactose to recover ricin with intact binding capacity. Ricin $^{125}$I was mixed with an appropriate amount of cold ricin and then covalently linked to TA-1, UCHT-1, or T101. Human bone narrow mononuclear cells, 40–80 × 10$^7$ total, were pretreated with 1000 ng labeled immunotoxin/ml (2–3 × 10$^3$ CPM) under standard pretreatment conditions (10$^7$ cells/ml in 100 nM lactose). The suspension was counted for gamma radioactivity prior to incubation to determine Total CPM. After 2 hours the cells were washed twice (RPMI 1640 + 100 mM lactose + 2% human serum albumin). Supernatants from the first and second washes and then the pellet were measured for radioactivity. A tube containing labeled IT with no cells present were counted as an additional control. The values were similar to those reported for Total CPM. Duplicate samples were measured. Data were expressed as CPM/culture. Standard deviations did not exceed 20% of mean values.

[b] % Total = $\frac{\text{CPM in pellet, 1st wash, or 2nd wash}}{\text{Total CPM present in culture following addition of } ^{125}\text{I-labeled IT}} \times 100$

[c] Equimolar mixture of TA-1-ricin, UCHT-1-ricin and T101-ricin totaling 1000 ng immunotoxin/ml.

table 1indicates that a mixture of cells treated with $^{125}$I-TUT showed 2385 CPM prior to washing, representing the total radioactivity present in the sample. After two hours the cells were washed twice. The first wash contained 96% of the radioactivity and the second, an additional 3%. The 6% radioactivity remaining in the pellet represents the amount of IT bound to the surface or internalized by the treated cell population. Since the first wash, second wash, and pellet contained 105% of the initial total activity, it is assumed that these percentages represent approximations.

3. Antibody Labeling

The advantage of labeling the MoAb before conjugation is less inactivation of the toxin moiety. The MoAb may be radiolabeled by the methods described above as referred to in immunotoxin labeling. Conjugation of toxin to the radiolabeled MoAb may be carried out as described above for one and two chain toxins.

II. EXAMPLES

A. In vitro Studies with RIT

A radioimmunotoxin (RIT) was prepared by conjugating T101 MoAb to ricin as described above and radio-labeling the conjugate with $^{125}$I by the iodine monochloride micro method. T101 recognizes a specific marker on CEM tumor cells or peripheral blood mononuclear cells (PBMC). Briefly, 500μg aliquots were labeled with 1.3 mCi of radionuclide and 5 equivalents of IC1 to a specific activity of 0.5 mCi/mg. Free iodine ions were removed by passage over a Dowex 1-X4 resin column. Human serum albumin (5%) was used as a protective protein.

CEM or PBMC were cultured in the presence of 0.1μg/ml $^{125}$I-labled t101-ricin under internalizing conditions (37° C. for 2 hr). Cells were then washed and the amount of cell-associated $^{125}$I-labeled IT remaining was measured.

Each sample was counted for one minute in a well-type gamma counter to determine total counts added, then washed 3 times in PBS/5% FCS and counted again. The percent reagent bound to the cells (% binding) was calculated from non-internalizing (4° C.) samples as:

% binding = $\frac{(\text{cpm in sample after washing} - \text{background}) \times 100}{(\text{cpm in sample before washing} - \text{background})}$ Table II shows that the percent binding of the $^{125}$I-labeled T101-ricin to CEM cells was dependent on the cell concentration, but 34% binding was measured when 6×10$^6$ cells were treated in 300μ. For PBMC, 27.5% binding was measured when 6×10$^6$/300μl were treated. Mouse splenocytes and Daudi cells which do not express the cell marker recognized by T101 did not bind T101-ricin.

TABLE 2

To measure the gain or loss of cell-associated RIT, samples were incubated under internalizing (37° C.) or non-internalizing (4° C.) conditions. The difference in counts associated with the cells at 4° C. and 37° C. was expressed as the % relative difference according to the following formula:

% relative difference $\frac{(\text{cpm internalized} - \text{bkg}) - 1}{(\text{cpm non-internalized} - \text{bkg})} \times 100$ If the value for the % relative difference is a positive number, it indicates that label was internalized. A negative value indicates counts were lost and that label was shed from the cell surface.

When 6×10$^6$ CEM cells were treated with labeled T101-ricin/lactose, the % relative difference was 32.5% (Table II), suggesting that $^{125}$I-T101 ricin was internalized. PBMC showed a low percent relative difference value (1.0), suggesting that label was neither shed nor rapidly taken up.

TABLE II

FATE OF $^{125}$I—T101 AND $^{125}$I—T101-RICIN AFTER MODULATION[a] ON CEM AND PBMC

| | | T101-Ricin/Lactose | | | | T101-MoAb | | | |
|---|---|---|---|---|---|---|---|---|---|
| Cells | Concentration | Temp. | cpm | % binding[b] | % rel. diff.[c] | Temp. | cpm | % binding | % rel. diff. |
| CEM | 6 × 10$^6$/300 ul | 37° C. | '45631 ± 20503[d] | 34.0 ± 7.0 | 32.5 ± 0.19 | 37° C. | 20263 ± 10522 | 17.2 ± 2.9 | 19.9 ± 0.21 |
| | | 4° C. | 35541 ± 13277 | | | 4° C. | 16309 ± 5517 | | |
| PBMC | 6 × 10$^6$/300 ul | 37° C. | 32102 ± 2321 | 27.5 ± 0.7 | 1.0 ± 0.11 | 37° C. | 11686 ± 8311 | 11.8 ± 7.8 | −33.8 ± 0.18 |
| | | 4° C. | 31828 ± 1289 | | | 4° C. | 17290 ± 12301 | | |
| mouse splenocytes | 6 × 10$^6$/300 ul | 37° C. | 668[e] | 0.6 | N.A. | 37° C. | 572 ± 543 | 0.5 ± 0.2 | N.A.[f] |
| | | 4° C. | 755[e] | | | 4° C. | 535 ± 465 | | |
| Daudi | 6 × 10$^6$/300 ul | 37° C. | 8366 ± 9417 | 3.0 ± 1.4 | N.A. | 37° C. | 1549 ± 743 | 2.3 ± 1.0 | N.A. |

TABLE II-continued

| | | FATE OF $^{125}$I—T101 AND $^{125}$I—T101-RICIN AFTER MODULATION$^a$ ON CEM AND PBMC | | | | | | |
|---|---|---|---|---|---|---|---|---|
| | | T101-Ricin/Lactose | | | | T101-MoAb | | |
| Cells | Concentration | Temp. | cpm | % binding$^b$ | % rel. diff.$^c$ | Temp. | cpm | % binding | % rel. diff. |
| | | 4° C. | 7940 ± 8327 | | | 4° C. | 1663 ± 911 | | |

$^a$To determine the fate of reagent after modulation, samples were incubated with IT or T101 for 30 min at 4° C. Samples were then transferred to 37° C. for 2 hr, washed 3 times, and counted in a gamma counter.
$^b$Percent binding was quantitated by incubating cells with IT or T101 for 2 hr at 4° C. Samples were counted in a gamma counter before and after washing. Percent binding was determined.
$^c$To determine whether counts were lost or gained during modulation, modulated samples were compared to non-modulated controls (4° C.). The relative difference in counts was determined.
$^d$Except where indicated, numbers represent mean values from 2-5 experiments.
$^e$Only one experiment shown.
$^f$N.A. = not applicable. Mouse splenocytes and Daudi served as negative controls and therefore have no relative difference value.

Using radiolabled T101 antibody, CEM demonstrated a positive % relative difference in cell associated T101 between internalized (37° C.) and non-internalized (4° C.) samples, indicating uptake. However, PBMC showed a negative relative value, suggesting shedding of label from the cell surface. Together these findings show that IT are internalized, whereas radiolabeled MoAb can be shed.

Figure 1A:
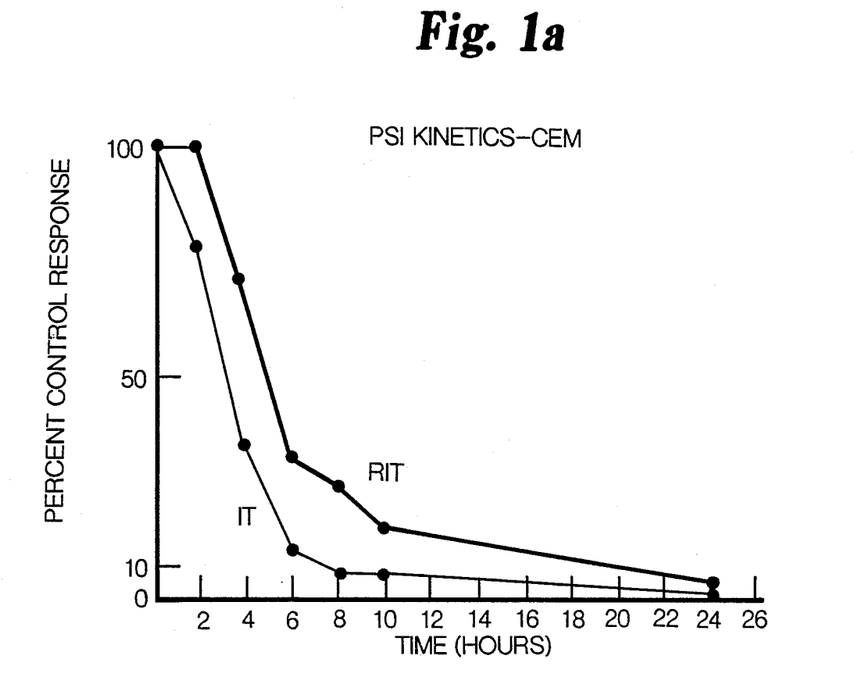
FIG. 1a, CEM cells treated with RIT or IT in the presence of lactose.

In addition to binding and internalization, the specific cytotoxicity and protein synthesis inhibition kinetics of T101-RIT were measured. These assays are important in establishing the ability of T101-RIT to kill tumor. CEM tumor cells (T101 positive) and Daudi (T101 negative) were used in the tests. RIT was found to be as effective as IT in the inhibition of protein synthesis of CEM cells (FIG. 1A).

Figure 1B:
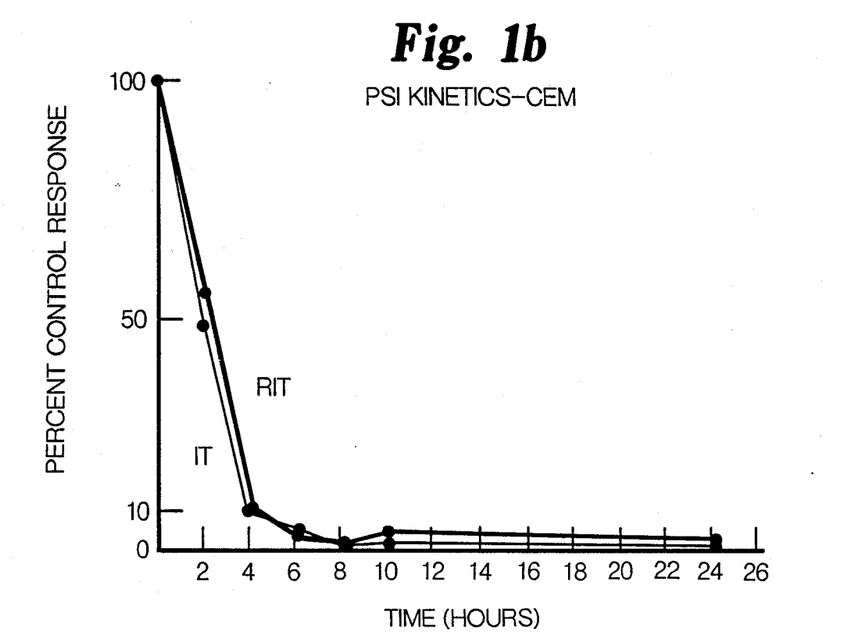
FIG. 1b, CEM cells treated with RIT or IT in the absence of lactose.
Figure 1C:
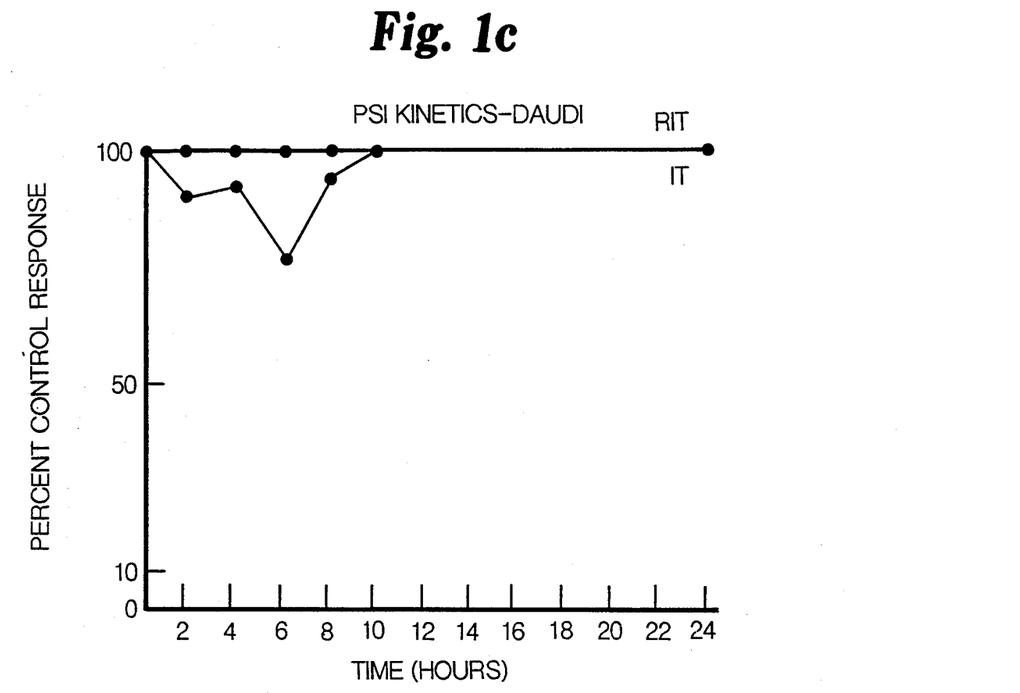
FIG. 1c, Daudi cells treated with RIT or IT in the presence of lactose.

In the presence of lactose, both RIT and IT at 0.1μg/ml inhibited protein synthesis to less than 40% of control value by 6 hours. Unlabeled IT showed slightly faster inhibition of protein synthesis, with little or no lag period as compared to RIT which showed a lag period of approximatley 2 hours. However, both reagents inhibited protein synthesis to less than 5% of controls by 24 hours. CEM incubated with RIT or IT in the absence of lactose showed a rapid decrease in $^3$H-leucine incorporation, indicating protein synthesis inhibition (FIG. 1B). BotH reagents decreased protein synthesis to 10% of controls by 4 hours. Daudi cells, when icubated in the presence of T101-IT or T101-RIT in the presence of lactose, showed no substantial decrease in protein synthesis throughout the 24 hour incubation period (FIG. 1C), indicating that the reagents were binding specifically via their antibody moiety.

Figure 1D:
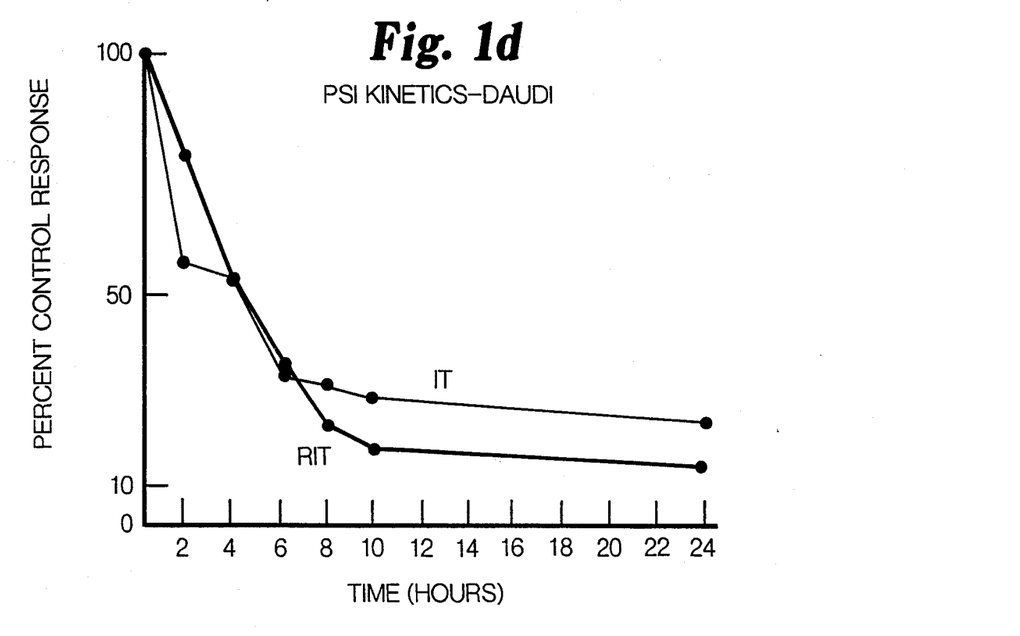
FIG. 1d, Daudi cells treated with RIT or IT in the absence of lactose.

However, when Daudi cells were incubated with RIT or IT in the absence of lactose (FIG. 1D), protein synthesis was inhibited to 50% of controls by 4 hours, and to less than 25% of controls by 24 hours. These results indicate that (1) RIT and IT demonstrate similar activity toward specific cell populations in vitro, and (2) RIT retain both toxicity and specificity comparable to unlabeled IT.

FIG. 1

Protein Synthesis Inhibition Kinetics

Representative experiments show protein synthesis inhibition (PSI) on CEM and Daudi cells incubated with IT or RIT. Washed cells ($2 \times 10^6$/200μl) were incubated with or without 0.1μg RIT or IT in luecine-free RPMI 1640 containing 10% heat-inactivated dialyzed FCS. Samples were treated as duplicates, one set of samples was incubated in 150 mM lactose and the other was not. All samples were incubated at 37° C. At designated intervals, aliquots of cells were diluted and 100μl aliquots ($10^5$ cells) were transferred to triplicate wells of flat bottom tissue culture plates. Each well was pulsed for 2 hours at 37° C. with 1-μCi $^3$H-leucine. Cells were then harvested, washed, and dried. $^3$H-leucine incorporation was determined using standard scintillation counting techniques. Results were expressed as percent control using the following formula:

$$\% \text{ control} = \frac{\text{cpm treated sample}}{\text{cpm untreated sample}} \times 100$$

Time plotted is the incubation time plus ½ the 2 hour $^3$H-leucine pulse. Six time points (1,3,5,7,9,23 hr) were assayed. Control cultures were incubated without RIT or IT. A. CEM cells treated with RIT or IT in the presence of lactose. B. CEM cells treated with RIT or IT in the absence of lactose. C. Daudi cells treated with RIT or IT in the presence of lactose. D. Daudi cells treated with RIT or IT in the absence of lactose.

B. In vivo Studies with RIT

The RIT reagent was tested against established CEM and Daudi xenografts in nude mice. Human tumors can be grown in athymic nude mice as a standard procedure for evaluation. Palpable tumors (0.25-0.99cm$^2$) were treated by intratumoral injection of 5μg RIT. Intratumoral injection of RIT was preceded by intravenous injection of 0.7 ml of 500 mM lactose, and the injected RIT was diluted into 500 mM lactose prior to injection into the animal. All tumor bearing animals were observed for several weeks, or until death of the animal.

We found RIT to be selectively toxic in tumor bearing mice (FIG. 2), showing a substantial antitumor effect in 6/8 animals tested. CEM tumors treated with RIT exhibited an area of local necrosis and scabbing 2-4 days after RIT treatment. The necrotic area would usually progress to an area of white fibrosis with little or no visible tumor growth remaining at the site. CEM control tumors, which received no RIT injection, continued to grow (0/5 regressions). Negative control Daudi tumors showed 2/10 little or no regression after treatment with T101-RIT (2/10 regressions) (data not shown). These tumors did not exhibit necrosis or scabbing at the area of injection, and continued growth in a manner similar to untreated controls.

When 0.5 milligram aliquots of T101-IT were labled with 1.3 millicurries of $^{125}$I using 5 equivalents of ICl, the resulting RIT had a specific activity of 0.5 mCi/mg. T101 when labeled in the same manner had a similar specific activity. The average percentage binding of T101-RIT to $6 \times 10^6$ CEM cells in vitro was 24.5%. The average binding of $^{125}$I labeled T101 to an equal number of CEM cells was 23.3%. The average binding of T101-RIT and $^{125}$I labeled T101 to an equal number of Daudi cells was 0.7% in both cases.

The blood half life of T101-RIT and $^{125}$I labeled T101 was determined following intravenous injection in groups of five normal BALB/c mice given lactose by serial eye bleeding. The mean blood half life of T101-RIT and $^{125}$I-labeled T101 were 26.6 and 86.6 hours respectively.

Biodistribution studies of T101-RIT in nude mice given intravenous lactose and bearing CEM tumors was studied four days after intratumoral injection. The highest concentration of T101-RIT was in tumor, with relatively small amounts in the various normal tissues. There was a higher concentration of T101-RIT in CEM tumors than Daudi tumors in animals given intravenous lactose. The concentration of T101-RIT in Daudi tumors was higher in animals not receiving lactose.

Figure 2:
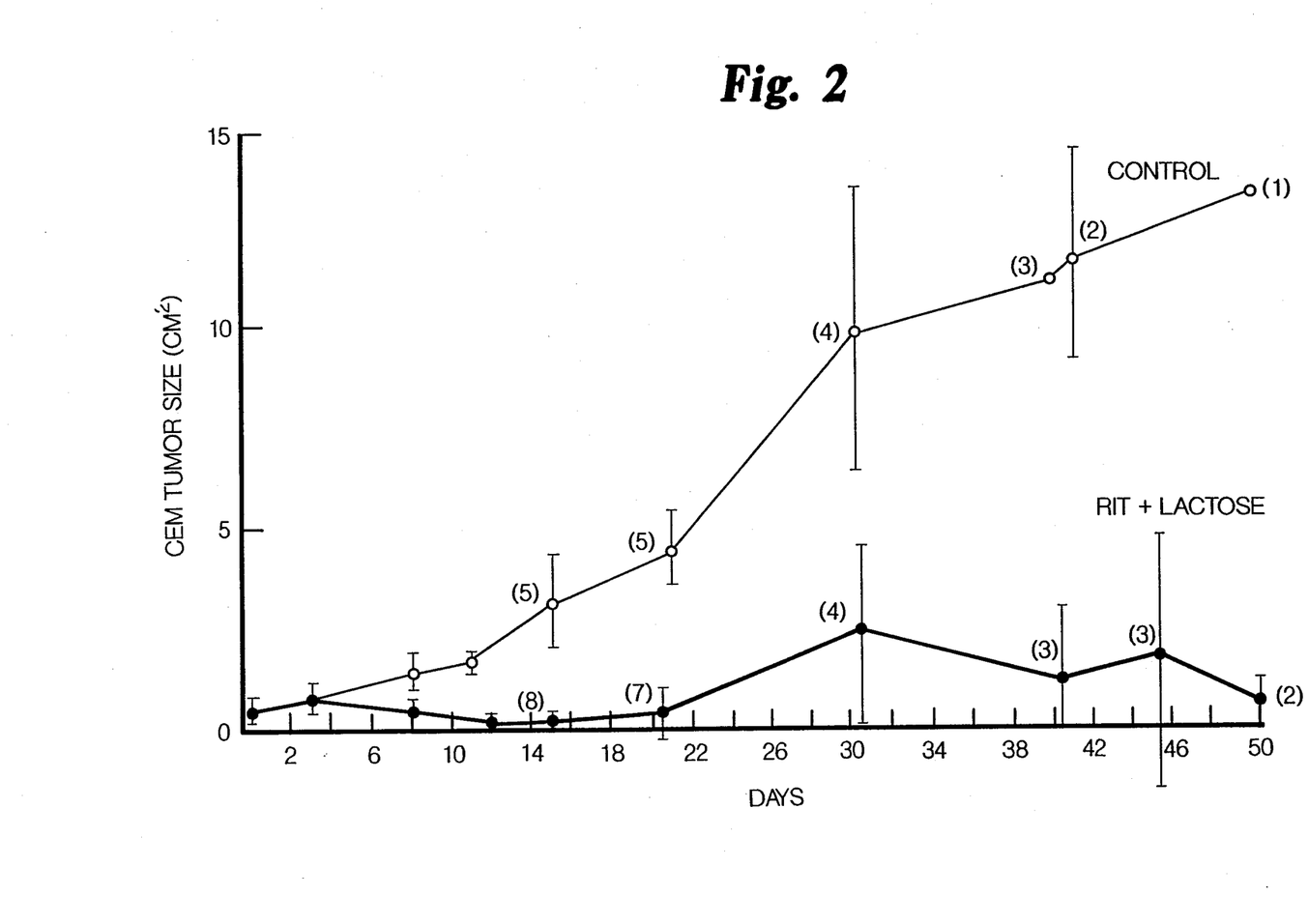
FIG. 2, growth of the CEM tumors with and without T101-RIT treatment plus lactose.

FIG. 2

Growth of CEM tumors with and without T101-RIT treatment plus lactose.

CEM cells ($10^7$ in 0.5 ml RPMI) were injected subcutaneously into the flank of nude mice. The mice were examined until palpable tumors were detected. Tumors were selected on the basis of size (0.25–0.99 cm$^2$) and were treated by intratumoral injection of 5µg RIT. The treatments were repeated 3 days after the first injection. At this time, however, animals received 2.5µg RIT as opposed to the 5µg given in the initial injection. Controls received no injections. Tumor size was determined by measuring two perpendicular diameters and calculating the approximate surface area as a product of the two measurements. Each point represents the mean of 2–8 tumor measurements, except in one case when only one mouse survived. Standard deviations ranged from 0.20–3.5. Tumor size (cm$^2$) is plotted against time (days).

Taken together, the results presented indicate that (1) IT can be radiolabeled with $^{125}$I and retain their toxicity and specificity, and (2) Rit plus lactose can selectively induce tumor regression in vivo in nude mice without causing grossly observable ricin or radiation toxicity in the treated animals.

C. Allogeneic Bone Marrow Transplantation (BMT)

In allogeneic BMT, normal T cells present in the donor bone marrow graft may immunologically respond against the cells of the immunosuppressed patient. This results in a severe, sometimes fatal pathological syndrome called Graft-Versus-Host-Disease (GVHD).

In studies with unlabeled IT it has been shown that IT when used to purge donor grafts of T-cells decreases the risk of severe GVHD. T101, an Ig2a monoclonal antibody binds to CD5, a 65KD glycoprotein on T cells. UCHTI, an IgG1 recognizes CD3, a 19KD determinant on T cells. TA1, an IgG2a recognizes CDW18, a two-chaiN non-covalently linked glycoprotein complex of 170 and 95KD also on T cells. These MoAbs have been linked to ricin and tested in vitro.

Human bone marrow cells pretreated with TA1-ricin have been found to be 100 fold more toxic to T-cells than to stem cells. Similar findings were observed for both UCHTI-ricin and T101-ricin. The mixture of all three IT (TUT), which was the most toxic in PHA (phytohemagglutinin) assays, was tested for its activity against stem cells of various lineages. Minimal toxicity was measured. It was found that 600 nanograms of IT-TUT/ml effectively inhibited PHA, MLR (mixed lymphocyte reaction), CML (cell medicated lympholysis), CTL (cytotoxic T-lymphocyte) activity and the natural killer cell (NK) activity. FIG. 1a provideS very strong support that RIT's prepared in accordance with the invention should be at least as effective as IT. Of course, the presence of the radionuclide provides a second killing agent to insure the eradication of all tumor cells.

Based on studies with mice, the LD$_{50}$ for TUT ricin RIT should be approximately $120 \times 10^{-6}$ grams per kilogram. Therefore, an RIT dose of approximately $1 \times 10^{-6}$ grams per kilogram should be at least 100 fold less toxic to patients than the LD$_{50}$ dose given to mice. Therefore, there should be a wide margin of safety with the use of RIT.

Patients treated with IT showed no signs of ricin toxicity and required less hospitalization time than patients that received conventional treatment for GVHD prophylaxis. Most notably, there was no severe GVHD in a study of 17 matched BMT patients proving the usefulness of this approach.

The advantage of employing RIT for purging are that they are (1) selective, (2) potent, (3) involve less manipulation than other current methods of T-cell depletion, (4) are uncomplicated and not very labor intense, (5) result in minimal loss of treated marrow, such that a maximum number of marrow cells can be returned to the immunosuppressed recipient, (6) can be prepared in large batches with a high degree of quality control, (7) remain stable for a year or longer and can be used to treat many sequential patients, and (8) have little effect on pluripotent stem cells. The inventors have prevented murine GVHD using this approach. This animal model has provided a useful guide for studies in man.

Monoclonal anti-Thy 1.2 against murine T-cells may be coupled to the potent toxin ricin and radiolabeled with iodine or other radionuclides in order to provide an effective RIT. Because the ricin RIT has a free galactose binding site, lactose should be added to the cell suspension containing RIT to block the native binding site of ricin so that RIT specificity is dictated by the antigen binding region of the MoAb. Based on work with IT's, such RIT's should be very potent reagents eliminating at least 1 to 2 logs of T-cells activity and should be at least 35 fold more active against T-cells but not stem cells. Thus, a safe dosage of RIT could be chosen since T-cells and not stem cells are killed.

D. Autologous Bone Marrow Transplant

RIT's may be utilized for ex vivo purging of neoplastic cells from patient bone marrow grafts. These autologous grafts are reintroduced into remission leukemic patients after aggressive supra lethal chemotherapy and irradiation. The objective of all strategies is to deplete neoplastic cells while leaving unharmed the pluripotent hematopoietic stem cells which repopulate the patient's marrow after reinfusion. Intact RIT's selectively eliminate antigen-positive targets without endangering engraftment and without causing intoxication.

Autologous marrow may be purged of residual leukemia cells without destroying hematopoietic stem cells by the use of RIT either in vivo or ex vivo. Ex vivo treatment with IT has been shown to eliminate most T or B cells present in human marrow without damaging the ability of the marrow to reconstitute lethally irradiated recipients. While the efficiency of IT to kill "the last" leukemic cells still remains an issue the even greater efficiency of an RIT should greatly increase the chances of successful treatment.

It has been reported that an IT can specifically eliminate more than 99.99% of clonogenic leukemic T cells even in the presence of excess human bone marrow. The use of RIT should eliminate even more leukemic T cells, possibly at a rate of greater than 5 logs or 99.999%, indicating that the RIT may be extremely useful for the ex vivo elimination of leukemic cells in autologous BMT. Until target determinants are completely identified, the use of RIT's will probably be more effective if they employ mixtures of RIT's having different monoclonal antibodies. Studies of four IT cocktails utilizing a concentration of only 300 nanograms per milliliter eliminated 4.1 logs of clonogenic MOLT 3 cells and activity. only 30% (0.2 logs) of pluripotent stem cell activity. Since this concentration represents only half a dose which has been used safely ex vivo to purge allogeneic marrow of GVHD causing cells, higher concentrations of the RIT cocktails may be usable for clinical applications.

In considering this invention it must be remembered that the disclosure is illustrative only and that the scope of the invention is illustrative only and by the appended claims.

What is claimed is:

1. A radioimmunotoxin consisting of the conjugation of a monoclonal antibody, toxin and radionuclide and having at least a 99% target cell killing efficiency.

2. The radioimmunotoxin of claim 1 wherein said toxins are selected from the group consisting of single chain, two chain and multiple chain toxins.

3. The radioimmunotoxin of claim 1 wherein said radionuclides are selected from the group consisting of beta emitting metallic radionuclides, alpha emitters and gamma emitters.

4. The radioimmunotoxins of claim 3 wherein said radionuclide is a radioactive iodine isotope.

5. The radioimmunotoxin of claim 3 wherein said radionuclide is selected from the group consisting of $^{88}Y$, $^{90}Y$ and $^{111}In$.

6. The radioimmunotoxin of claim 1 wherein said monoclonal antibody is in the form of the fragments F(ab')2 and Fab.

* * * * *

UNITED STATES PATENT AND TRADEMARK OFFICE
CERTIFICATE OF CORRECTION

PATENT NO. : 4,831,122
DATED : May 16, 1989
INVENTOR(S) : Buchsbaum et al

It is certified that error appears in the above-identified patent and that said Letters Patent is hereby corrected as shown below:

Col 5, line 19, delete "claculated" and insert -calculated-

Col. 8, line 17, delete "exchage" and insert - exchange -

Col. 9, line 18, delete "table lindicates" and insert - Table 1 indicates"

Col. 11, line 35, delete "approximatley" and insert - approximately -

Col. 11, line 40, delete "BotH" and insert - Both -

Col. 11, line 41, delete "icubated" and insert -incubated-

Col. 14, line 2, delete "provideS" and insert - provides -

Signed and Sealed this

Thirteenth Day of February, 1990

Attest:

JEFFREY M. SAMUELS

Attesting Officer

Acting Commissioner of Patents and Trademarks